United States Patent

Onoe et al.

Patent Number: 4,849,138
Date of Patent: Jul. 18, 1989

[54] METHOD OF PRODUCING ALKALI METAL BENZENESULFINATES

[75] Inventors: Akira Onoe, Himeji; Masao Kawamura; Kunioki Kato, both of Akashi; Masato Yoshikawa, Kobe; Hirokazu Kagano, Tannancho, all of Japan

[73] Assignee: Seitetsu Kagaku Co., Ltd., Hyogo, Japan

[21] Appl. No.: 84,572

[22] Filed: Aug. 12, 1987

[30] Foreign Application Priority Data

Aug. 13, 1986 [JP] Japan .................. 61-190790

[51] Int. Cl.$^4$ .......................................... C07C 145/00
[52] U.S. Cl. ..................... 562/125; 568/28; 568/30
[58] Field of Search ............... 568/28, 30; 260/513.7

[56] References Cited

U.S. PATENT DOCUMENTS 3,006,963 10/1961 Buc ........................ 568/28

FOREIGN PATENT DOCUMENTS 1471966 1/1967 France ...................... 568/28
0100018 8/1975 Japan ...................... 260/513.7

Primary Examiner—Alan Siegel
Attorney, Agent, or Firm—Wenderoth, Lind & Ponack

[57] ABSTRACT

A method of producing alkali metal benzenesulfinates having the general formula of

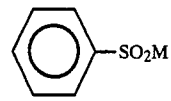

wherein M represents Na or K, which comprises: reacting nitrophenylphenyl sulfones having the general formula of

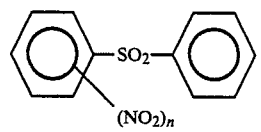

wherein n is an integer of 1 or 2, with alkali metal thiophenolates having the general formula of

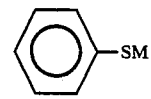

in solvents.

The reaction produces also nitrophenylphenyl sulfides as by-products in equimolar amounts to the alkali metal benzenesulfinates, and the oxidation of the sulfides provides the starting nitrophenylphenyl sulfones.

A method of producing the nitrophenylphenyl sulfones is also provided wherein the sulfides are oxidized with hydrogen peroxide in the presence both of water-soluble tungstates or molybdates and of phase transfer catalysts in a two-phase heterogeneous solvent.

33 Claims, No Drawings

METHOD OF PRODUCING ALKALI METAL BENZENESULFINATES

This invention relates to a method of producing alkali metal benzenesulfinates, and also to a method of producing nitrophenylphenyl sulfones usable as starting materials in the production of alkali metal benzenesulfinates.

Alkali metal benzenesulfinates are useful intermediate raw materials for the production of organic sulfones and sofoxides important in organic synthetic industry.

Up to date a variety of methods are already known to produce alkali metal benzenesulfinates. These prior methods include, for example, a method in which benzenesulfonyl chloride is reduced with sodium sulfite as described in A. D. Barnard et al., J. Chem. Soc., 1957, 4673. However, according to this method, sodium sulfinate is produced in solutions together with water-soluble compounds such as sodium sulfate, sodium chloride or sodium benzenesulfonate, so that it is very difficult to separate sodium benzenesulfinate from the by-products by crystallization on account of closeness of the solubilities in water of all these compounds. Therefore, it is generally preferred that the resultant solution is then acidified with a mineral acid to convert the alkali metal benzenesulfinates into the free acid, and then the free acid is separated by filtration or is extracted with organic solvents. This method is, however, at disadvantage from the industrial standpoint in that is requires handling of the free acid which is chemically rather unstable as well as it needs the aforesaid additional steps that incur higher production cost.

A further method is also known in which benzene is sulfinated with sulfur dioxide in the presence of aluminum chloride as a catalyst, as described in Nippon Kagaku Zasshi, 1968, 89(8), 810. This method needs the catalyst in amounts equivalent to benzene used, and the catalyst cannot be recovered after the reaction, which makes the method uneconomical. A still further method is known in which 2,4-dinitrophenylphenyl sulfone is reacted with potassium hydroxide to provide potassium benzenesulfinate, as described in C. N. Kharash et al., J. Org. Chem., 19, 1704 (1954). However, this method has disadvantages in that the separation of potassium benzenesulfinate from by-products, potassium 2,4-dinitrophenolate is difficult.

As described above, the methods hitherto known have disadvantages in many respects, and there is known no method that is advantageously applicable to the industrial production of alkali metal benzenesulfinates.

The present inventors have made extensive investigations to establish an improved method of producing alkali metal benzenesulfinates more efficiently and less expensively than the prior methods, and found out that alkali metal benzene-sulfinates are readily obtained in high yields by the reaction of nitrophenylphenyl sulfones with alkali metal thiophenolates in solvents.

It is, therefore, an object of the invention to provide a novel method of producing alkali metal benzenesulfinates.

It is also an object of the invention to provide a novel method of producing nitrophenylphenyl sulfones which are usable as starting materials in the production of alkali metal benzenesulfinates.

According to the invention, there is provided a method of producing alkali metal benzenesulfinate having the general formula of

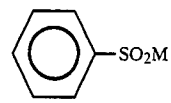

wherein M represents Na or K, which comprises: reacting nitrophenylphenyl sulfones having the general formula of

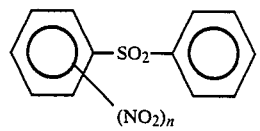

wherein n is an integer of 1 or 2, with alkali metal thiophenolates having the general formula of

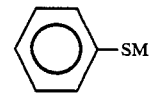

in solvents.

The nitrophenylphenyl sulfones used in the invention include 2- and 4-nitrophenylphenyl sulfone and 2,4-dinitro-phenylphenyl sulfone. The alkali metal thiophenolates used in the invention include sodium and potassium salts, which provide sodium and potassium benzenesulfinate, respectively, in almost quantitatively by the reaction with the aforesaid nitrophenylphenyl sulfones. In the reaction, the alkali metal thiophenolates are usually used in amounts of about 0.8–1.2 moles per, preferably in amounts equivalent to, the nitrophenylphenyl sulfones used.

The reaction is carried out in solvents usually composed of a mixture of water and organic solvents that dissolve therein nitrophenylphenyl sulfones used and are inert to the reaction. The organic solvents usable may be either water-soluble or water-insoluble, and include, for example, lower aliphate alcohols of 1–5 carbons such as methanol, ethanol or isopropanol, aliphatic hydrocarbons such as hexane or heptane, aromatic hydrocarbons that may carry one or more of lower alkyls each of 1–3 carbons such as benzene, toluene, xylene, ethylbenzene or isopropyl-benzene, lower alkyl esters of lower aliphatic carboxylic acids having in total 3–8 carbons such as methyl acetate, ethyl acetate or methyl propionate, nitrated aromatic hydrocarbons such as nitrobenzene or nitrotoluene.

The reaction may be carried out either in homogeneous solvents or in two-phase heterogeneous solvents depending upon the organic solvents used. By way of example, a mixture of water and water-soluble organic solvents such as methanol or ethanol is a homogeneous sovent, whereas a mixture of water and water-insoluble or slightly water-soluble organic solvents such as ethyl acetate, toluene, nitrobenzene or nitrotoluene is a two-phase heterogeneous solvent.

Water-soluble or water-miscible aliphatic alcohols such as methanol or ethanol may be used alone as a solvent in the reaction since such alcohols are capable of dissolving not only thiophenol and alkali metal hydroxides but also nitrophenylphenyl sulfones therein. However, thiophenol and alkali metal hydroxides are reacted with each other therein to produce in situ alkali thiophenolates, and the reaction also produces water, so that if the alcohols alone are used as a solvent, they inevitably include water therein.

The reaction may be carried out in manners that are not specifically limited, but it is generally preferred that the reaction is carried out by adding a solution of alkali thiophenolates in water, methanol or hydrous methanol, to a solution of nitrophenylphenyl sulfones in organic solvents as hereinbefore mentioned under stirring, and then the resultant mixture is stirred, if desired, at elevated temperatures, for about 1–10 hours. The reaction temperature is usually in the range of about 30°–100° C. When the reaction temperature is too low, the reaction proceeds too slowly to be industrially workable, whereas when the reaction temperature is too high, undesired side reactions take place to decrease the yields of the objective compounds and the selectivity of the reaction. The alkali metal thiophenolates may be prepared by, for example, reacting thiophenol with sodium or potassium hydroxide in equimolar amounts in water, methanol or a mixture of these.

When a two-phase heterogeneous solvent is used, the reaction is preferably carried out in the presence of phase transfer catalysts, which are already known per se. The phase transfer catalysts usable in the invention include, for example, tetraalkylammoniums, such as tetramethylammonium chloride, tetraethylammonium chloride, tetrabutylammonium bromide or trioctylmethylammomium chloride, tetraalkyl-ammonium hydrogen sulfates such as tetrabutylammonium hydrogen sulfate, benzyltrialkylammoniums such as benzyl-trimethylammonium chloride, benzyltrietylammonium chloride, benzyldimethyllaurylammonium chloride or benzyldimethyl-tetradecylammonium chloride, and dibenzyldialkylammoniums such as dibenzyldimethylammonium chloride or dibenzyldimethylammonium chloride. The use of the phase transfer catalysts accelerates the reaction and increases the yields of the alkali metal benzenesulfinates.

The phase transfer catalysts are used in amounts of about 0.1–5 %, preferably 0.2–1 % by weight, based on the weight of the alkali metal thiophenolates used. The use of too small amounts is ineffective to accelerate the reaction, while the use of too large amounts is uneconomical.

When the reaction is carried out in a homogeneous solvent, the solvent is concentrated after the reaction, water and organic solvents such as toluene are added to the resultant concentrate, and the aqueous solution is separated and concentrated to dryness, to provide alkali metal benzene-sulfinates as white crystals. As by-products, nitrophenyl-phenyl sulfides are recovered from the organic solution.

When the reaction is carried out in a heterogeneous solvent, the reaction mixture is separated into an aqueous solution and an organic solution after the reaction, the aqueous solution is water with organic solvents, for example, toluene, and is then concentrated to dryness, to provide alkali metal benzenesulfinates as white crystals. The nitrophenylphenyl sulfides are recovered from the organic solution.

The reaction of nitrophenylphenyl sulfones with alkali metal thiophenolates according to the invention is shown below.

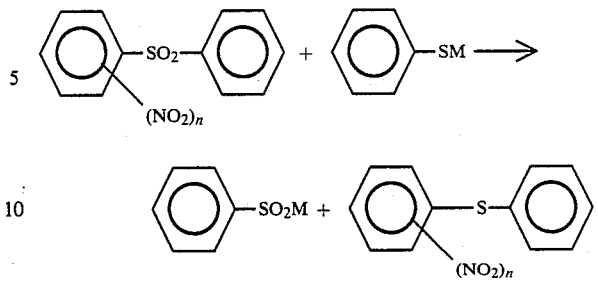

wherein M represents Na or K, and n is an integer of 1 or 2.

As shown above, the reaction produces, in addition to the alkali metal benzenesulfinates, nitrophenylphenyl sulfides, as by-products, which can be oxidized with oxidizing agents to the corresponding nitrophenylphenyl sulfones initially used. In this regard, nitrophenylphenyl sulfones that have one or two nitro groups on one of the aromatic nuclei provide both alkali metal benzenesulfinates and nitrophenylphenyl sulfones in high yields, in almost equimolar amounts.

A variety of oxidizing agents are usable for oxidizing nitrophenylphenyl sulfides into the corresponding nitrophenyl-phenyl sulfones. The oxidizing agents usable in the invention include, for example, hydrogen peroxide, peracids such as peracetic acid, hydroperoxides, halogens such as chlorine or bromine, ozone, oxygen with transition metal catalysts, potassium peroxysulfate, potassium permanganate, dinitrogen tetroxide, sodium metaperiodate, osmium (VIII) oxide, ruthenium (VIII) oxide, sodium or potassium dichromate and nitric acid.

However, hydrogen peroxide is most preferred as oxidizing agents since the oxidation of the nitrophenylphenyl sulfides therewith provides the corresponding nitrophenyl-phenyl sulfones almost quantitatively.

Therefore, as an important aspect of the invention, the recovered nitrophenylphenyl sulfides produced as by-products can be reused in the reaction after the oxidation. More specifically, the recovered nitrophenylphenyl sulfides are oxidized to the nitrophenylphenyl sulfones, and the sulfones are anew reacted with the alkali metal thiophenolates, to provide the alkali metal benzenesulfinates and again the nitrophenylphenyl sulfides. Therefore, the nitrophenylphenyl sulfones as raw materials are needed to initially carry out the reaction, however, if needed, only supplementary amounts of nitrophenylphenyl sulfones are needed in the succeeding reactions, and hence according to the invention, the alkali metal benzenesulfinates can be produced much less expensively than the prior known methods ever known.

According to the invention, there is further provided a novel method of producing nitrophenylphenyl sulfones by the oxidation of nitrophenylphenyl sulfides.

According to the invention, there is further provided a method of producing nitrophenylphenyl sulfones having the general formula of

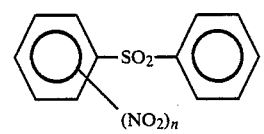

wherein n is an integer of 1 or 2, which comprises: oxidizing nitrophenylphenyl sulfides having the general formula of

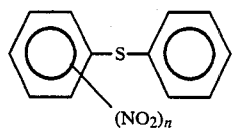

wherein n is an integer of 1 or 2, with hydrogen peroxide in the presence both of oxidizing catalysts selected from the group consisting of water-soluble tungstates and molybdates and of phase transfer catalysts in a two-phase heterogeneous solvent.

The oxidation reaction is carried out in a two-phase heterogeneous solvent, which is composed of water and water-insoluble or slightly water-soluble organic solvents. Any water-insoluble or slightly water-soluble organic solvents are usable when they are capable of dissolving therein nitrophenylphenyl sulfides and are inert to the reaction. The organic solvents usable include, for example, aliphatic hydrocarbons such as hexane, heptane or octane, aromatic hydrocarbons such as benzene, toluene, xylene, ethylbenzene or isopropylbenzene, alicyclic hydrocarbons such as cyclohexane or ethylcyclohexane, and nitrated aromatic hydrocarbons such as nitrobenzene or nitrotoluene. Alkyl esters of acetic acid or higher carboxylic acids are also usable as organic solvents, such as ethyl acetate propyl acetate, butyl acetate, amyl acetate or ethyl propionate.

In the oxidation reaction, hydrogen peroxide is used as oxidizing agents in amounts of not less than about 2 moles, preferably in the range of about 2-2.5 moles, per mole of nitrophenylphenyl sulfides used. There is no need to use hydrogen peroxide in large excess amounts.

The tungstates and molybdates used as oxidizing catalysts in the reaction are water-soluble, and include alkali metal salts such as lithium, sodium or potassium salts, alkaline earth metal salts such as magnesium salts, and ammoniums. Preferred catalysts are therefore lithium tungstate, sodium tungstate, potassium tungstate, magnesium tungstate, ammonium tungstate, sodium molybdate, potassium molybdate and ammonium molybdate.

The oxidizing catalyst is used in amounts of about 0.5-5% by weight, preferably of about 1-2 % by weight, based on the weight of the nitrophenylphenyl sulfides used. The use of too small amounts is ineffective to accelerate the reaction, whereas the use of too large amounts is uneconomical.

In the oxidizing reaction of the invention, phase transfer catalysts are used together with the oxidizing catalysts. The phase transfer catalysts hereinbefore described are also usable in the reaction. Preferred phase transfer catalysts used include, for example, tetraalkylammoniums such as tetramethylammonium chloride, tetraethylammonium chloride, tetrabutylammonium bromide or trioctylmethylammonium chloride, tetraalkylammonium hydrogen sulfates such as tetrabutylammonium hydrogen sulfate, benzyltrialkylammoniums such as benzyltrimethyl-ammonium chloride, benzyltrietylammonium chloride, benzyl-dimethyllaurylammonium chloride or benzyldimethyltetradecylammonium chloride, and dibenzyldialkylammoniums such as dibenzyldiemthylammonium chloride or dibenzyldiethylammonium chloride.

The phase transfer catalysts are used usually in amounts of about 0.1-3 % by weight, preferably of about 0.2-1 % by weight, based on the weight of nitrophenylphenyl sulfides used. The use of too small amounts is ineffective to accelerate the reaction, whereas the use of too large amounts is uneconomical.

The oxidation reaction is preferably carried out in acidic or neutral conditions by adding a small amount of inorganic strong acids such as sulfuric acid or hydrochloric acid to the reaction mixture. Namely, the reaction is carried out preferably at a pH of not more than about 7, and most preferably at a pH of about 1-7. However, when ammonium hydrogen sulfates such as tetrabutylammonium hydrogen sulfate are used as a phase transfer catalyst, there is no need to add an inorganic strong aid to the reaction mixture to adjust the pH thereof at acidic regions since the ammonium hydrogen sulfates themselves are strongly acidic.

Although the invention is not limited in theory or mechanism of the reaction, the oxidizing catalysts are converted into acid forms, i.e., tungstic acid or molybdic acid in acidic or neutral conditions, and the acids react with the phase transfer catalysts and transfer from the water phase to the organic phase in the reaction mixture, thereby to effectively catalyze the oxidation of the nitrophenyl-phenyl sulfides into the corresponding nitrophenyl-phenyl sulfones. More specifically, it is likely that the tungstates or molybdates are oxidized into peroxotungstic acid or peroxomolybdic acid, respectively, in acidic or neutral conditions, and the peroxoacids react with the phase transfer catalysts to transfer to the organic phase, thereby effectively catalyzing the oxidation of the sulfides to the sulfones.

On the other hand, when the reaction is carried out in alkaline conditions, the oxidizing catalysts remain in the water phase in the form of the salts in the reaction mixture, and it is likely that the salts do not react with the phase transfer catalysts, thereby being prevented from transferring from the water phase to the organic phase where the substantial oxidation reaction is carried out.

The oxidizing reaction is carried out usually at temperatures of about 50°-90° C., preferably at about 60°-80° C. When the reaction temperature is too low, the reaction proceeds too slowly, and when the reaction temperature is too high, the selectivity of the reaction and the yields of the sulfones are low.

The reaction manners are not specifically limited, however, it is preferred that the reaction is carried out by dissolving nitrophenylphenyl sulfides in the organic solvents and adding to the resultant solution the oxidizing catalysts, the phase transfer catalysts, and then, if necessary, an inorganic strong acid, and then by adding dropwise thereto aqueous solution of hydrogen peroxide under stirring at temperatures of about 60°-90° C. After the completion of the reaction, the reaction mixture is separated into an organic solution and aqueous solution, and the organic solution is concentrated to dryness, to provide nitrophenylphenyl sulfones in high yields. The resultant sulfones may be purified by recrystallization.

The invention will be understood more readily with reference to the following examples; however these examples are intended to illustrate the invention only and are not to be construed as limitation to the invention.

EXAMPLE 1

(i) Production of Sodium Benzenesulfinate and Recovery of 2- Nitrophenylphenyl Sulfide An amount of 26.3 g (0.1 mole) of 2-nitrophenylphenyl sulfone was dissolved in 100 g of methanol in a 300 ml capacity four-necked flask provided with a stirrer, a thermometer, a dropping funnel and a reflux condensor. An amount of 11.0 g (0.1 mole) of thiophenol and 4.0 g (0.1 mole) of sodium hydroxide were dissolved in 30 g of methanol. The resultant methanol solution of sodium thiophenolate was added to the aforesaid solution of 2-nitrophenylphenyl sulfone, and the reaction was carried out at 60° C. for 4 hours.

After the reaction, methanol was concentrated, toluene and water were added to the concentrate, and the aqueous solution was separated from the organic solvent. The aqueous solution was concentrated to dryness, to provide 16.1 g (97.1 % yield) of sodium benzenesulfinate as white crystals. The purity was found 99.0 % by liquid chromatography.

The removal of toluene from the organic solution by distillation provided 22.6 g (96.7 % yield) of 2-nitrophenyl-phenyl sulfide as yellow crystals. The purity was found 98.8 % by liquid chromatography.

(ii) Oxidation of 2-Nitrophenylphenyl Sulfide and Reuse

An amount of 21.1 g (0.09 mole) of the recovered 2-nitrophenylphenyl sulfide was plaed in a 200 ml capacity flask together with 83.3 g of acetic acid and heated to 50° C. to provide a uniform solution. The solution was further heated to 85° C., and 26.2 g of a 35% aqueous solution of hydrogen peroxide (0.27 mole) were dropwise added to the solution of the sulfide over 30 minutes while the solution was maintained at 85° C.

After stirring the 5 hours at 85° C., the resultant reaction mixture was left standing at room temperature, the resultant precipitates were filtered and dried, to provide 23.0 g (95.4 % yield) of 2-nitrophenylphenyl sulfone, mp. 146.9°-148.6° C., which was found 98.2 % in purity by liquid chromatography.

An amount of 21.4 g (0.08 mole) of the thus obtained 2-nitrophenylphenyl sulfone was dissolved in 80 g of methanol, and was reacted with sodium thiophenolate in the same manner as above-mentioned.

After the reaction, methanol was concentrated, toluene and water were added to the concentrate, and the aqueous solution was separated from the organic solution. The aqueous solution was then concentrated to dryness, to provide 12.7 g (95.8 % yield) of sodium benzenesulfinate as white crystals. The purity was found 99.1 % by liquid chromatography.

2- Nitrophenylphenyl sulfide was recovered from the toluene solution.

EXAMPLE 2

(i) Production of Sodium Benzenesulfinate and Recovery of 2- Nitrophenylphenyl Sulfide A mixtue of 100 g of ethyl acetate and 100 g of water was used as a solvent, and the reaction was carried out in the same manner as in Example 1 in the presence of 0.1 g of benzyltriethylammonium chloride as a phase transfer catalyst.

After the reaction, the reaction mixture was left standing at room temperature, the resulting aqueous solution was separated from the ethyl acetate solution containing 2-nitrophenylphenyl sulfide, and concentrated to dryness, to provide 13.7 g (82.7 % yield) of sodium benzenesulfinate as white crystals, which was found 99.1 % in purity by liquid chromatography.

The removal of ethyl acetate by distillation from the ethyl acetate solution provided 22.4 g (95.8 % yield) of 2-nitrophenylphenyl sulfide as yellow crystals. The sulfide was found 98.9 % in purity by liquid chromatography.

(ii) Oxidation of 2-Nitrophenylphenyl Sulfide and Reuse

An amount of 21.0 g (0.09 mole) of the recovered 2-nitrophenylphenyl sulfide was oxidized with 26.2 g (0.27 mole) of a 35 % aqueous solution of hydrogen peroxide in the same manner as in Example 1. After the reaction, the reaction mixture was cooled, and resulting precipitates were filtered and dried, to provide 23.1 g (95.9 % yield) of 2-nitrophenylphenyl sulfone as white crystals, mp. 147.0°-148.7 ° C. The purity was found 98.4 % by liquid chromatography.

An amount of 21.4 g (0.08 mole) of the thus obtained 2-nitrophenylphenyl sulfone was dissolved in a mixture of 80 g of ethyl acetate and 80 g of water, and was reacted with sodium thiophenolate in the same manner as in Example 1.

After the reaction, ethyl acetate was concentrated, toluene and water were added to the concentrate, and the aqueous solution was separated from the organic solution. The aqueous solution was concentrated to dryness, to provide 12.5 g (94.2 % yield) of sodium benzenesulfinate as white crystals. The purity was found 99.0 % by liquid chromatography.

2- Nitrophenylphenyl sulfide was recovered from the toluene solution.

EXAMPLE 3

4-Nitrophenylphenyl sulfone was used in place of 2-nitrophenylphenyl sulfone and otherwise the reaction was carried out in the same manner as in Example 1.

After the reaction, methanol was concentrated, toluene and water were added to the concentrate, and the aqueous solution was separated from the organic solution containing 4-nitrophenylphenyl sulfide as by-products. The aqueous solution was concentrated to dryness, to provide 14.8 g (88.5 % yield) of sodium benzenesulfinate as while crystals. The purity was found 98.2% by liquid chromatography.

EXAMPLE 4

4- Nitrophenylphenyl sulfone and a solvent as a mixture of 100 g of toluene and 100 g of water were used in place of 2-nitrophenylphenyl sulfone and methanol, respectively, and the reaction was carried out in the presence of 0.1 g of tetrabutylammonium hydrogen sulfate as a phase transfer catalyst otherwise in the same manner as in Example 1.

After the reaction, the reaction mixture was left standing at room temperature, the aqueous solution was separated from the toluene solution containing 4-nitrophenylphenyl sulfide as by-products. The aqueous layer was concentrated to dryness, to provide 14.6 g (88.4 % yield) of sodium benzenesulfinate as white crystals. The purity was found 99.4 % by liquid chromatography.

EXAMPLE 5

(i) Production of Sodium Benzenesulfinate and Recovery of 2- Nitrophenylpheny Sulfide 4-Nitrophenylphenyl sulfone and a solvent composed of a mixture of 100 g of nitrobenzene and 100 g of water were used in place of 2-nitrophenylphenyl sulfone and methanol, respectively, and the reaction was carried out in the presence of 0.1 g of tetrabutylammonium hydrogen sulfate as a phase transfer catalyst otherwise in the same manner as in Example 1.

After the reaction, the reaction mixture was left standing at room temperatures, the aqueous solution was separated from the nitrobenzene solution containing 4-nitrophenylphenyl sulfide. The aqueous layer was concentrated to dryness, to provide 15.3 g (92.5 % yield) of sodium benzene sulfinate as white crystals. The purity was found 99.3 % by liquid chromatography.

The nitrobenzene solution was concentrated by distilation to dryness, to provide 22.6 g (96.5 % yield) of 4-nitro-phenylphenyl sulfide, which was found 98.7 % in purity by liquid chromatography.

(ii) Oxidation of 4-Nitrophenylphenyl Sulfide and Reuse

An amount of 21.1 g (0.09 mole) of the recovered 4-nitrophenylphenyl sulfide was oxidized with hydrogen peroxide in the same manner as in Example 1. After the reaction, the reaction mixture was cooled, and resulting precipitates were filtered and dried, to provide 23.1 g (96.0 % yield) of 4-nitrophenylphenyl sulfone as white crystals, mp. 141.4°-142.9° C. The purity was found 98.5 % by liquid chromatography.

An amount of 21.4 g (0.08 mole) of the thus obtained 4-nitrophenylphenyl sulfone was dissolved in a two phase solvent composed of a mixture of 80 g of nitrobenzene and 80 g of water, and was reacted with sodium thiophenolate in the same manner as in Example 1.

After the reaction, the resultant aqueous solution was separated from the organic solvent. The aqueous solution was concentrated to dryness, to provide 12.6 g (95.2 % yield) of sodium benzenesulfinate as white crystals. The purity was found 99.2 % by liquid chromatography.

EXAMPLE 6

An amount of 5.6 g (0.1 mole) of potassium hydroxide was used in place of sodium hydroxide, and the reaction was carried out otherwise in the same manner as in Example 1.

After the reaction, methanol was concentrated, toluene and water were added to the concentrate, and the aqueous solution was separated from the organic solution containing 2-nitrophenylphenyl sulfide. The aqueous solution was concentrated to dryness, to provide 15.0 g (82.4 % yield) of sodium benzenesulfinate as white crystals. The purity was found 99.0 % by liquid chromatography.

EXAMPLE 7

An amount of 30.8 g (0.1 mole) of 2,4-dinitrophenylphenyl sulfone was used in place of 2-nitrophenylphenyl sulfone, and the reaction was carried out otherwise in the same manner as in Example 1.

After the reaction, methanol was concentrated, toluene and water were added to the concentrate, and the aqueous solution was separated from the toluene solution containing 2,4-dinitrophenylphenyl sulfide. The aqueous solution was then concentrated to dryness, to provide 13.8 g (83.4 % yield) of sodium benzenesulfinate as white crystals. The purity was found 99.2 % by liquid chromatography.

EXAMPLE 8

Ethanol was used as a solvent in place of methanol, and the reaction was carried out otherwise in the same manner as in Example 1.

After the reaction, ethanol and methanol were concentrated, toluene and water were added to the concentrate, and the aqueous solution was separated from the toluene solution. The aqueous solution was then concentrated to dryness, to provide 16.0 g (96.7 % yield) of sodium benzenesulfinate as white crystals. The purity was found 99.2 % by liquid chromatography.

The removal of toluene from the toluene solution provided 22.5 g (96.1 % yield) of 2-nitrophenylphenyl sulfide. The purity was found 99.1 % by liquid chromatography.

EXAMPLE 9

An amount of 46.2 g (0.2 mole) of 2-nitrophenylphenyl sulfide was dissolved under heating in 200 g of toluene in a 500 ml capacity four-necked flask provided with a stirrer, a thermometer, a dropping funnel and a reflux condensor, and there were added thereto 1 g of sodium tungstate dihydrate and 2 g of tetrabutylammonium hydrogen sulfate. To the resultant mixture were then dropwise added 40.9 g (0.42 mole) of 30 % of weight aqueous solution of hydrogen peroxide at temperatures of about 80° C. under stirring, and the reaction was carried at the temperature for 3 hours. The pH of the reaction mixture was found about 1.

After the completion of the reaction, the reaction mixture was separated into a toluene solution and an aqueous solution, and the toluene solution was concentrated to dryness, to provide 51.8 g (97.8 % yield) of 2-nitrophenylphenyl sulfone as pale yellow crystals. The purity was found 99.5% by liquid chromatography.

EXAMPLE 10

An amount of 46.2 g (0.2 mole) of 2-nitrophenylphenyl sulfide was dissolved under heating in 200 g of toluene in a 500 ml capacity four-necked flask provided with a stirrer, a thermometer, a dropping funnel and a reflux condensor, and there were added thereto 1 g of sodium tungstate dihydrate, 2 g of benzyltrimethylammonium chloride, and 1.5 g of sulfuric acid in this order. To the resultant mixture were then added dropwise 40.9 g (0.42 mole) of aqueous hydrogen peroxide at temperatures of about 80° C. under stirring, and the reaction was carried at the temperature for 3 hours. the pH of the reaction mixture was found about 1.

After the completion of the reaction, the reaction mixture was separated into a toluene solution and an aqueous solution, and the toluene solution was concentrated to dryness, to provide 51.6 g (97.6 % yield) of 2-nitrophenylphenyl sulfone as pale yellow crystals. The purity was found 99.5 % by liquid chromatography.

EXAMPLE 11

Trioctylmethylammonium chloride was used in amounts of 2 g as phase transfer catalysts in place of tatrabutyl-ammonium hydrogen sulfate, and 1.5 g of sulfuric acid were added to a toluene solution of the sulfide together with hydrogen peroxide, and the reaction was carried out otherwise in the same manner as in Example 9.

After the reaction, the reaction mixture was separated into a toluene solution and an aqueous solution, and the toluene solution was concentrated to dryness, to provide 51.8 g (97.4 % yield) of 2-nitrophenylphenyl sulfone as pale yellow crystals. The purity was found 99.0 % by liquid chromatography.

EXAMPLE 12

Benzyldimethyllaurylammonium chloride was used in amounts of 2 g as phase transfer catalysts in place of tetra-butylammonium hydrogen sulfate, and 1.5 g of sulfuric acid were added to a toluene solution of the sulfide together with hydrogen peroxide, and the reaction was carried out otherwise in the same manner as in Example 9.

After the reaction, the reaction mixture was separated into a toluene solution and an aqueous solution, and the toluene solution was concentrated to dryness, to provide 51.7 g (97.4 % yield) of 2-nitrophenylphenyl sulfone as pale yellow crystals. The purity was found 99.2 % by liquid chromatography.

EXAMPLE 13

An amount of 46.2 g (0.2 mole) of 4-nitrophenylphenyl sulfide was used in place of 2-nitrophenylphenyl sulfide, and the reaction was carried out otherwise in the same manner as in Example 9.

After the reaction, the reaction mixture was separated into a toluene solution and an aqueous solution, and the toluene solution was concentrated to dryness, to provide 51.9 g (97.7 % yield) of 4-nitrophenylphenyl sulfone as pale yellow crystals. The purity was found 99.1 % by liquid chromatography.

EXAMPLE 14

An amount of 46.2 g (0.2 mole) of 4-nitrophenylphenyl sulfide was used in place of 2-nitrophenylphenyl sulfide, and nitrobenzene was used as organic solvents in place of toluene, and the reaction was carried out otherwise in the same manner as in Example 9.

After the reaction, the reaction mixture was separated into a nitrobenzene solution and an aqueous solution, and the nitrobenzene solution was heated and concentrated, and then cooled. The resultant solids were separated by filtration, washed with methanol, and then dried, to provide 50.3 g (95.2 % yield) of 4-nitrophenylphenyl sulfone as pale yellow crystals. The purity was found 99.7 % by liquid chromatography.

EXAMPLE 15

An amount of 46.2 g (0.2 mole) of 4-nitrophenylphenyl sulfide was used in place of 2-nitrophenylphenyl sulfide, and 1 g of ammonium molybdate was used in place of sodium tungstate, and the reaction was carried out otherwise in the same manner as in Example 9.

After the reaction, the reaction mixture was separated into a toluene solution and an aqueous solution, and the toluene solution was concentrated to dryness, to provide 51.5 g (97.5 % yield) of 4-nitrophenylphenyl sulfone as pale yellow crystals. The purity was found 99.7% by liquid chromatography.

EXAMPLE 16

Amount of 55.2 g (0.2 mole) of 2,4-dinitrophenyl-phenyl sulfide was used in place of 2-nitrophenylphenyl sulfide, and the reaction was carried out otherwise in the same manner as in Example 9.

After the reaction, the reaction mixture was separated into a toluene solution and an aqueous solution, and the toluene solution was concentrated to dryness, to provide 60.4 g (97.3 % yield) of 2,4-dinitrophenylphenyl sulfone as yellow crystals. The purity was found 99.3 % by liquid chromatography.

EXAMPLE 17

An amount of 55.2 g (0.2 mole) of 2,4-dinitrophenylphenyl sulfide was used in place of 2-nitrophenylphenyl sulfide, and 2 g of benzyldimethyltetradecylammonium chloride in place of tetrabutylammonium hydrogen sulfate, and the reaction was carried out otherwise in the same manner as in Example 9.

After the reaction, the reaction mixture was separated into a toluene solution and an aqueous solution, and the toluene solution was concentrated to dryness, to provide 60.5 g (97.2 % yield) of 2,4-dinitrophenylphenyl sulfone as yellow crystals. The purity was found 99.1 % by liquid chromatography.

EXAMPLE 18

Benzyltrimethylammonium chloride was used in amounts of 2 g as phase transfer catalysts in place of tatrabutyl-ammonium hydrogen sulfate, and the reaction was carried to otherwise in the same manner as in Example 9. Since there was added no sulfuric acid to the reaction mixture, the pH of the reaction mixture was found about 7.

After the reaction, the reaction mixture was separated into a toluene solution and an aqueous solution, and the toluene solution was analyzed by liquid chromatography. The toluene solution was found to contain 2-nitrophenylphenyl sulfone in amounts of 85.6 % and 2-nitrophenylphenyl sulfoxide (by-products) in amounts of 14.4 %.

EXAMPLE 19

Benzyltrimethylammonium chloride was used in amounts of 2 g as phase transfer catalysts in place of tatrabutyl-ammonium hydrogen sulfate, and 1.5 g of sodium hydroxide were added to a toluene solution of the sulfide together with hydrogen peroxide, and the reaction was carried out in an alkaline condition at a pH of about 14 otherwise in the same manner as in Example 9.

After the reaction, the reaction mixture was separated into a toluene solution and an aqueous solution, and the toluene solution was analyzed by liquid chromatography. The toluene solution was found to contain 2-nitrophenylphenyl sulfide (unreacted) in amounts of 73.2 %, 2-nitrophenylphenyl sulfoxide (by-products) in amounts of 15.5 %, and 2-nitro-phenylphenyl sulfone in amounts of 11.3 %.

What is claimed is:

1. A method of producing alkali metal benzenesulfinates having the general formula of

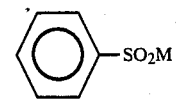

where M represents Na or K, which comprises: reacting nitrophenylphenyl sulfones having the general formula of

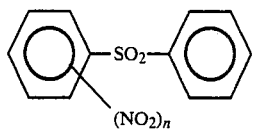

wherein n is an integer of 1 or 2, with alkali metal thiophenolates having the general formula of

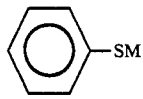

in solvents, to provide the alkali metal benzenesulfinates together with nitrophenylphenyl sulfides having the general formula of

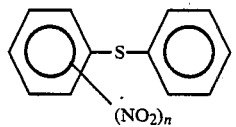

wherein n is an integer of 1 or 2.

2. The method as claimed in claim 1 wherein the solvent is a homogeneous one composed of water and water-soluble lower aliphatic alcohols.

3. The method as claimed in claim 2 wherein the lower aliphatic alcohols are methanol or ethanol.

4. The method as claimed in claim 1 wherein the reaction is carried out in methanol or ethanol.

5. The method as claimed in claim 1 wherein the solvent is a two-phase heterogeneous one composed of a mixture of water and water-insoluble or slightly water-soluble organic solvents.

6. The method as claimed in claim 5 wherein the organic solvents are aliphatic hydrocarbons, aromatic hydrocarbons, nitrated aromatic hydrocarbons or carboxylic acid esters.

7. The method as claimed in claim 5 wherein the organic solvents are toluene, nitrobenzene or ethyl acetate.

8. The method as claimed in claim 1 wherein the reaction is carried out in a two-phase heterogeneous solvent composed of a mixture of water and water-insoluble or slightly water-soluble organic solvents in the presence of a phase transfer catalyst.

9. The method as claimed in claim 8 wherein the organic solvents are aliphatic hydrocarbons, aromatic hydrocarbons, nitrated aromatic hydrocarbons or carboxylic acid esters.

10. The method as claimed in claim 8 wherein the organic solvents are toluene, nitrobenzene or ethyl acetate.

11. The method as claimed in claim 8 wherein the phase transfer catalysts are tetraalkylammoniums or benzyltrialkyl-ammoniums or dibenzyldialkylammoniums.

12. The method as claimed in claim 8 wherein the phase transfer catalysts are tetraalkylammonium halides or benzyl-trialkylammonium halides or dibenzyldialkylammonium halides.

13. The method as claimed in claim 8 wherein the phase transfer catalysts are tetraalkylammonium hydrogen sulfates.

14. The method as claimed in claim 1 wherein nitrophenyl-phenyl sulfides having the general formula of

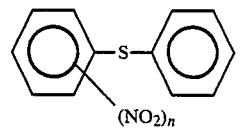

wherein n is an integer of 1 or 2, produced as by-products in the reaction, is oxidized to the nitrophenylphenyl sulfones for reuse in the reaction.

15. A method of producing alkali metal benzenesulfinates having the general formula of

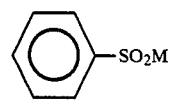

wherein M represents Na or K, which comprises: reacting nitrophenylphenyl sulfones having the general formula of

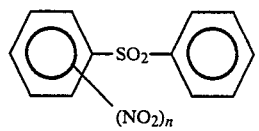

wherein n is an integer of 1 or 2, with alkali metal thiophenolates having the general formula of

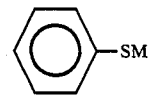

in a homogeneous or a first two-phase heterogeneous solvent, to provide the alkali metal benzenesulfinates together with nitrophenylphenyl sulfides having the general formula of

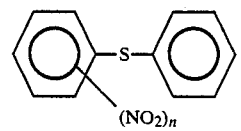

wherein n is an integer of 1 or 2; and oxidizing the nitrophenylphenyl sulfides to the nitrophenylphenyl sulfones for use in the reaction with the alkali metal thiophenolates, with hydrogen peroxide in the presence both of oxidizing catalysts selected from the group consisting of water-soluble tungstates and molybdates and of phase transfer catalysts in acidic or neutral conditions in a second two-phase heterogeneous solvent.

16. The method as claimed in claim 15 wherein the first homogeneous solvent is composed of water and water-soluble lower aliphatic alcohols.

17. The method as claimed in claim 16 wherein the lower aliphatic alcohols are methanol or ethanol.

18. The method as claimed in claim 15 wherein the reaction of the sulfones with the thiophenolates is carried out in methanol or ethanol.

19. The method as claimed in claim 15 wherein the first two-phase heterogeneous solvent is composed of a mixture of water and water-insoluble or slightly water-soluble organic solvents.

20. The method as claimed in claim 19 wherein the organic solvents are aliphatic hydrocarbons, aromatic hydrocarbons, nitrated aromatic hydrocarbons or carboxylic acid esters.

21. The method as claimed in claim 19 wherein the organic solvents are toluene, nitrobenzene or ethyl acetate.

22. The method as claimed in claim 15 wherein the reaction of the sulfones with the thiophenolates is carried out in the presence of a phase transfer catalyst.

23. The method as claimed in claim 22 wherein the phase transfer catalysts are tetraalkylammoniums, benzyltrialkylammoniums or dibenzyldialkylammoniums.

24. The method as claimed in claim 22 wherein the phase transfer catalysts are tetraalkylammonium halides, benzyltrialkylammonium halides or dibenzyldialkylammonium halides.

25. The method as claimed in claim 22 wherein the phase transfer catalysts are tetraalkylammonium hydrogen sulfates.

26. The method as claimed in claim 15 wherein the second two-phase heterogeneous solvent is composed of a mixture of water and water-insoluble or slightly water-soluble organic solvents.

27. The method as claimed in claim 26 wherein the organic solvents are aliphatic hydrocarbons, aromatic hydrocarbons, nitrated aromatic hydrocarbons or carboxylic acid esters.

28. The method as claimed in claim 26 wherein the organic solvents are toluene, nitrobenzene or ethyl acetate.

29. The method as claimed in claim 15 wherein the phase transfer catalysts are tetraalkylammoniums, benzyltrialkylammoniums or dibenzyldialkylammoniums.

30. The method as claimed in claim 15 wherein the phase transfer catalysts are tetraalkylammonium halides, benzyltrialkylammonium halides or dibenzyldialkylammonium halides.

31. The method as claimed in claim 15 wherein the phase transfer catalysts are tetraalkylammonium hydrogen sulfates.

32. The method as claimed in claim 15 wherein the tungstates are sodium tungstate, potassium tungstate or ammonium tungstate.

33. The method as claimed in claim 15 wherein the molybdates are sodium molybdate, potassium molybdate or ammonium molybdate.

* * * * *